United States Patent
Crispin et al.

(10) Patent No.: US 7,687,270 B1
(45) Date of Patent: Mar. 30, 2010

(54) HYPERGOLIC FUEL LEAK DETECTOR AND ALARM SYSTEM, COLORIMETRIC WITH OPTICAL READER

(75) Inventors: Kevin W. R. Crispin, Loma Mar, CA (US); Terrence R. McGinnis, Boulder Creek, CA (US); Robert J. Gerenser, Milpitas, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 1250 days.

(21) Appl. No.: 10/712,588

(22) Filed: Nov. 12, 2003

Related U.S. Application Data

(60) Provisional application No. 60/425,790, filed on Nov. 12, 2002.

(51) Int. Cl.
*G01N 35/00* (2006.01)
(52) U.S. Cl. .................. 436/55; 436/139; 436/164; 422/55; 422/68.1; 422/61
(58) Field of Classification Search ............ 436/55, 436/139, 164; 422/55, 58.61, 68.1, 119
See application file for complete search history.

(56) References Cited

U.S. PATENT DOCUMENTS

| | | | | |
|---|---|---|---|---|
| 5,301,538 A | * | 4/1994 | Recla | 73/40.5 R |
| 5,747,348 A | * | 5/1998 | Jaduszliwer et al. | 436/106 |

OTHER PUBLICATIONS

"Assaying the Rayleigh Intensity Remote Leak Detection Technique", Sandra Clements, 2001, NASA/ASEE Summer Faculty Fellowship Program.*
"Advanced Development of Ground Instrumentation as a Key Strategy in Improving the Safety and Efficiency of Space Shuttle Checkout and Launch", Helms et al., Apr. 1996, A Paper Presented to the Thirty Third Space Congress, Coco Beach, Florida.*

* cited by examiner

*Primary Examiner*—Lyle A Alexander
(74) *Attorney, Agent, or Firm*—McDermott Will & Emery LLP

(57) ABSTRACT

A system for transporting fuel exhibits increased safety. The system includes a fuel leak detector including: a colorimetric chemical monitor configured to change color in response to presence of a fuel or fuel component, an optical reader configured to monitor a color of the chemical monitor, and an alarm system configured to provide an alarm when a color of the chemical monitor changes by a predetermined amount.

19 Claims, 15 Drawing Sheets

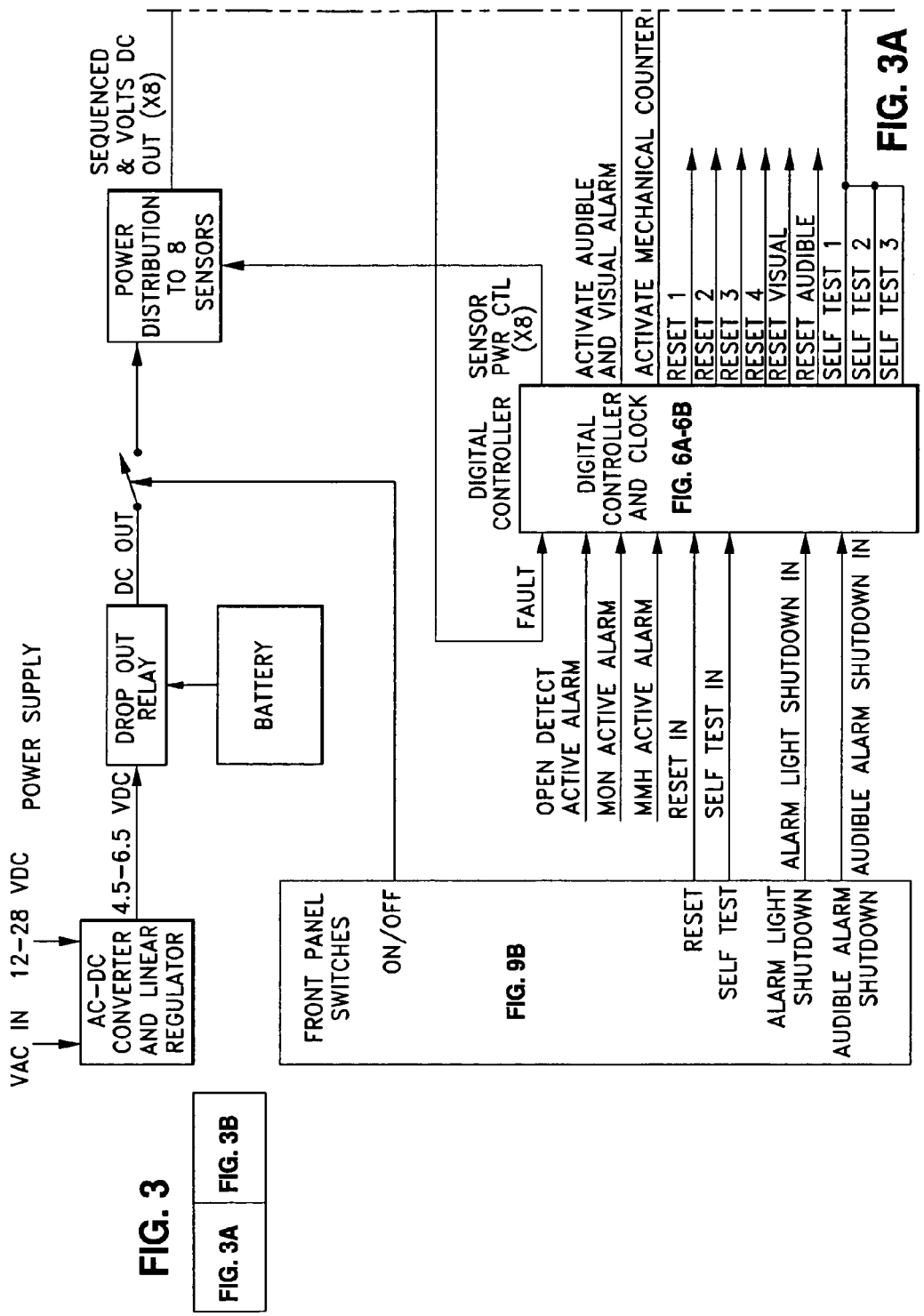

HYPERGOLIC FUEL LEAK DETECTOR AND ALARM SYSTEM, COLORIMETRIC WITH OPTICAL READER

CROSS-REFERENCE TO RELATED APPLICATION

The instant patent application claims priority from U.S. provisional patent application No. 60/425,790 filed Nov. 12, 2002 and hereby incorporated by reference for all purposes.

STATEMENT AS TO RIGHTS TO INVENTIONS MADE UNDER FEDERALLY SPONSORED RESEARCH OR DEVELOPMENT

Work described herein has been developed in performance of U.S. Department of Defense contracts control nos. 700bg1082002 and 70bga762010 The United States Government may therefore have certain rights in the invention.

BACKGROUND OF THE INVENTION

The Tactical High Altitude Area Defense (THAAD) system utilizes hypergolic fuel components which are stored adjacent to each other in preparation for use, and which operate (ignite) upon mixing. Transportation and storage of such hypergolic fuel or loaded propulsion systems require active sensing and remote alarming to a centralized area, in order to advise personnel of possible leaks. Distinguishing the presence of the hypergolic fuel components is thus desirable to promote appropriate hazardous safety response.

Colorimetric (color change reagent) chemical monitors or detectors are used throughout military and commercial industry as elements of safety alarm systems. These devices are typically designed to monitor exposure over relatively short terms, such as up to eight hours. Known calorimetric systems are also normally limited to an ambient temperature range of about +/−20 degrees.

Another aspect of such conventional calorimetric detection systems is that they are typically read manually. Manual reading relies on the human eye to read and compare the color change in order to determine concentration and/or exposure levels. Using the human eye to read the amount of color change can be imprecise and subjective. Moreover, manually read detectors can not be interfaced with area alarms to protect the safety of others, or to provide central resource response to hazardous conditions over a larger area.

Other conventional active detection systems utilize a reagent-impregnated paper tape that is slowly unreeled in front of a transmission spectrometer. However, such systems are typically bulky, consume substantial amounts of power, and do not operate over an extensive environmental temperature range.

Accordingly, there is a need in the art for methods and devices permitting detection the presence and concentration of the components of hypergolic fuel systems.

BRIEF SUMMARY OF THE INVENTION

Embodiments of devices and methods in accordance with the present invention enable the detection and discrimination of hypergolic fuel components (derivatives of hydrazine and nitrogen tetroxide) at below 100 ppmv, to thereby provide an alarm warning before this concentration limit is exceeded as indicative of a leak in the fuel system. An embodiment of the device in accordance with the present invention is principally designed as a safety sensor to alert personnel that hypergolic materials have leaked from fuel storage containers into secondary containment. Discrimination between the hypergolic fuel components can then determine the appropriate hazardous chemical response.

Embodiments of methods and devices in accordance with the present invention may function at least over the temperature range from about −46° C. to about +71° C. The detector operates by measuring a color change (calorimetric) in a substrate that has been impregnated with one or more chemical reagents. A visible detection system sends a signal to a central processing system when preset concentrations are exceeded. If these preset concentrations are exceeded, a control module activates alarm functions.

An embodiment of a transportation system in accordance with the present invention, comprises, a fuel leak detector comprising a calorimetric chemical monitor configured to change color in response to presence of a fuel, and an optical reader configured to monitor a color of the chemical monitor. An alarm system is in electronic communication with the fuel leak detector and configured to provide an alarm when a color of the chemical monitor changes by a predetermined amount.

An embodiment of a method in accordance with the present invention for detecting leakage of a hypergolic fuel system, comprises, providing a calorimetric chemical monitor, and providing an optical reader. Intensity of reflected light from the colorimetric chemical monitor is sensed by the optical reader. An occurrence of a fuel leak is determined when the intensity of reflected light drops below a predetermined threshold.

An embodiment of a method in accordance with the present invention for identifying a fuel leak, comprises, generating a voltage based upon comparison of a reference voltage with a voltage generated by a detector receiving light reflected from the surface of a substrate impregnated with a reagent reactive with a fuel component.

These and other embodiments of the present invention, as well as its advantages and features, are described in more detail in conjunction with the text below and attached figures.

DESCRIPTION OF THE INVENTION

Embodiments in accordance with the present invention actively monitor for the presence of hypergolic fuel components, in the form of hydrazine and its derivatives, or in the form of nitrogen tetroxide and its derivatives. The detector then determines the concentration of each target compound. The presence and concentration of each chemical class is monitored by determining the change in intensity of light reflected from a surface of a reagent-impregnated target. The greater the color change due to reaction between the reagents and the target compounds, the greater the absorption of light and the reduction in observed reflected light.

In accordance with one embodiment of the present invention, chemical reagents of interest are adsorbed onto a porous element of the detector. In accordance with one embodiment of the present invention, the porous element comprises a disc formed from Whatman No. 4 grade filter paper. Mercurous chloride/methylcellulose reagent may be adsorbed into one region of the paper disc. N-phenylanthranilic acid/titanium dioxide reagent may be adsorbed into another region of the paper disc.

The mercurous chloride/methylcellulose reagent present in the detector element may react selectively with monomethylhydrazine (MMH) and its derivatives to effect a color change from white to black. The magnitude of this color change is proportional to the extent of reaction between the reagent and the hypergolic fuel component.

Similarly, N-phenylanthranilic acid/titanium dioxide reagent present in the detector element may react selectively with mixed oxides of nitrogen (MON) such as nitrogen tetroxide and its derivatives, to effect a color change from white to yellow. Again the magnitude of this color change is also proportional to the extent of reaction between the reagent and the hypergolic fuel component.

Integrating the target compounds in the colorimetric sensor may increase the sensitivity of the detector. The chemical reagents impregnating the disk will fully react with any target chemical species that contact the reagent, with virtually no reverse reaction. When the reagent has reacted, the color will be fully changed. Such a color change will occur either if a slow leak occurs over a long period, or if a fast leak occurs more rapidly.

The active portion of the detector element analyzes the extent of color change of the calorimetric detector, and then calculates concentration of the relevant fuel components through comparison to a predetermined detector reference voltage. In accordance with one embodiment of the present invention, the active portion of the detector element may use blue light having a wavelength of about 450 nm from a light emitting diode (LED) to measure fuel component concentration.

Figure 1:
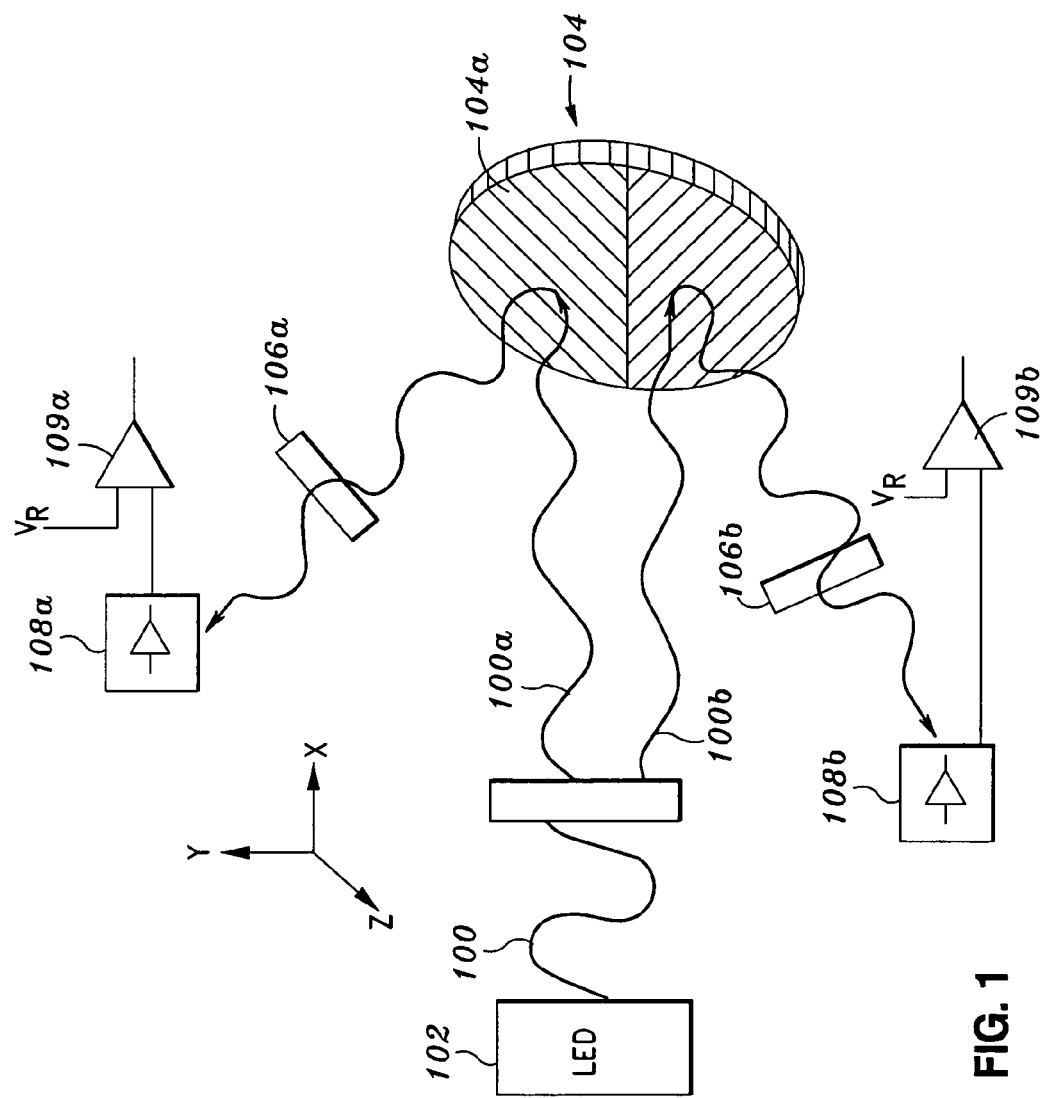
FIG. 1 shows a schematic view of active detection of hypergolic fuel components in accordance with an embodiment of the present invention.

As shown in the simplified schematic view of FIG. 1, light 100 transmitted from LED 102 is split into two paths 100a and 100b. One path 100a reflects off of first portion 104a of surface of the reagent-impregnated porous detector element 104, passing through first optical notch filter 106a onto first silicon optical detector 108a. First optical detector 108a is in electronic communication with first comparator 109a.

Second light path 100b reflects off of second portion 104b of the surface of the reagent-impregnated porous detector element 104, passing through second optical notch filter 106b onto second silicon optical detector 108b. Second optical detector 108b is in electronic communication with second comparator 109b. Both first and second comparators 109a-b are in electrical communication with predetermined reference voltage $V_R$.

Initially, when no hypergolic fuel components are present, light reflected from the surface of the porous detector element causes detectors 108a-b to output a voltage equal to $V_R$. Subsequently, when one or more hypergolic fuel components are present, one or both of the reagents experiences a color change. Light is correspondingly absorbed at the surface of the detector element, reducing the amount of light reaching the respective detector 108a-b. In response, the relevant detector elements 108a or 108b output a reduced voltage. Comparators 109a-b in turn output an increased voltage to a control module (not shown in FIG. 1).

When the reference voltage is matched or exceeded by the voltage output from the detector, the control module in turn sends a signal to the central alarm module. Voltage from the detector is a measure of the extent of the chemical reaction occurring on the reagent-impregnated disks of the detector. It will take approximately 0.5 milligrams of fuel or oxidizer to fully react with the chemical reagent to result in a full color change that results in the signal exceeding the reverence voltage.

Figure 2:
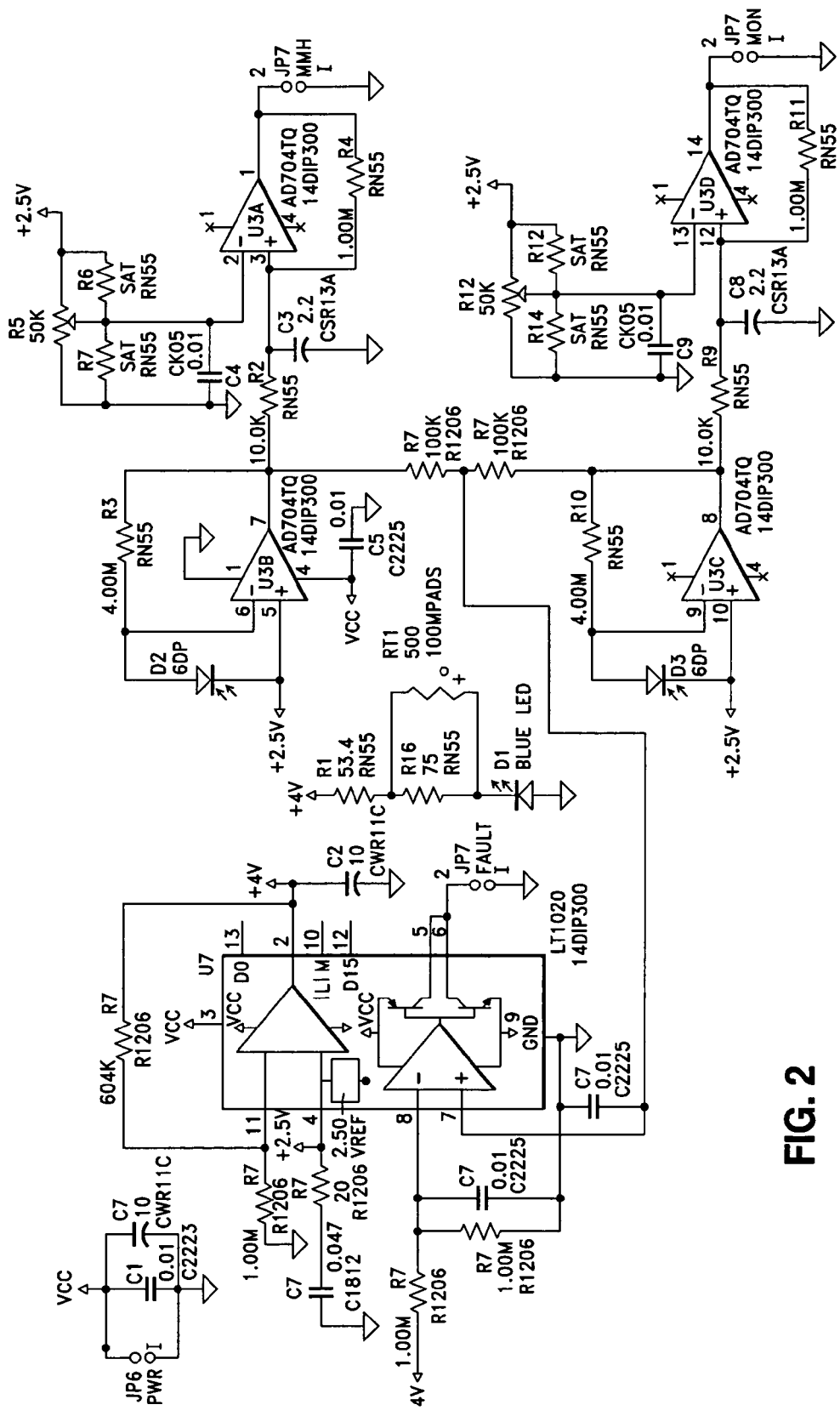
FIG. 2 shows a circuit diagram of electronic components of one embodiment of an active detection element of a system in accordance with the present invention.

FIG. 2 shows a circuit schematic of the electronics of the detector element. Blue light emitted from diode D1 is reflected off of the surface of the impregnated porous material. Photodiode D2 receives light reflected from the surface of the portion of the disc impregnated with mercurous chloride/methylcellulose reagent. Photodiode D3 receives light reflected from the surface of the portion of the disc impregnated with N-phenylanthranilic acid/titanium dioxide reagent.

The resulting voltage from diodes D2 and D3 is communicated to nodes 3 and 12 of comparators U3A and U3D respectively. A reference voltage of +2.5 V is supplied to second nodes 2 and 13 of comparators U3A and U3D respectively.

Deviation of the voltage received at the first nodes, from the reference voltage received at the second nodes, in turn results in generation of an output voltage of comparators U3A and U3D. This output voltage can then be sensed to indicate the presence of one or both of the hypergolic fuel components.

The performance of optical components, typically a light-emitting diode (LED) light source as well as of electronic components, may be affected by temperature. Through selection of components with characteristic positive and negative temperature coefficients, the effect of temperature upon performance can be minimized, resulting in a voltage signal vs. temperature slope of about zero. Minimizing the temperature effect allows the detection threshold to be reduced. A lower detection threshold in turn reduces the time for detection and increases the sensitivity of the device. Passive compensation for temperature effects simplifies the architecture of the device, reduces power consumption, and enhances the robustness of the device in a variety of environments.

Figure 3B:
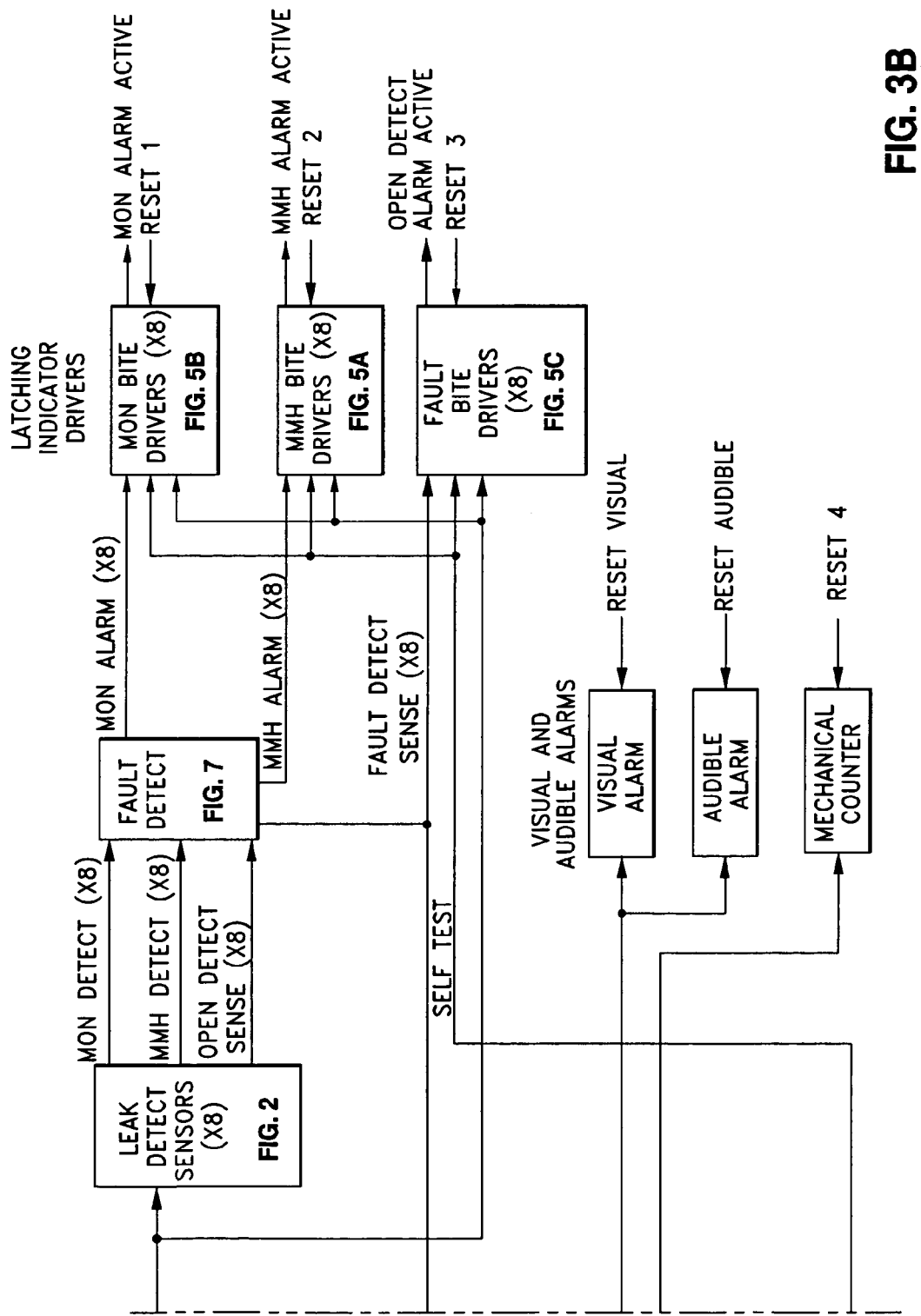
FIG. 3 shows a simplified logic diagram of an embodiment of a detection system in accordance with the present invention.
Figure 4:
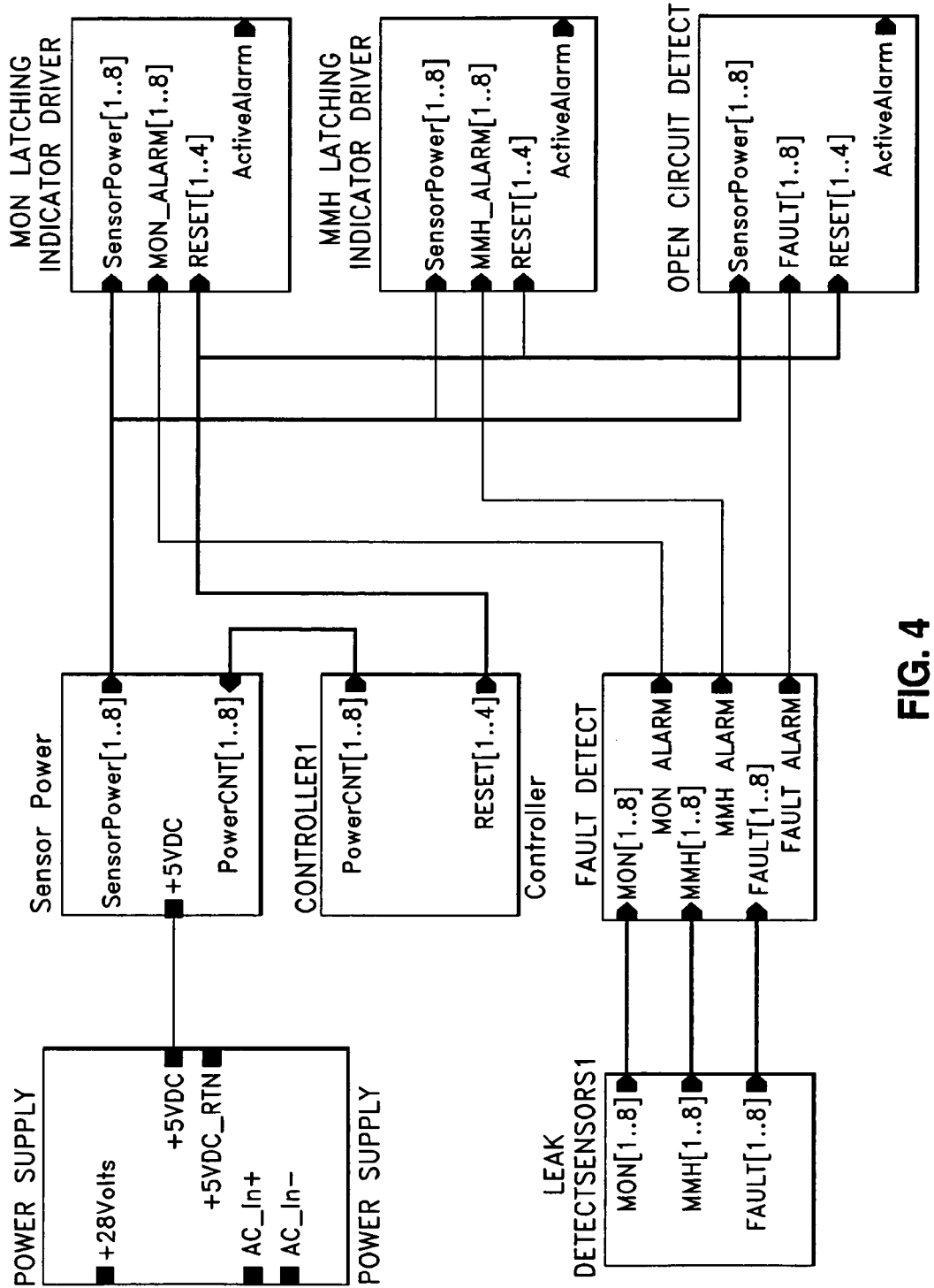
FIG. 4 shows a simplified block diagram of the embodiment of a detection system shown in FIG. 3.

FIG. 3 illustrates a simplified logic diagram of one embodiment of a detector system in accordance with the present invention. FIG. 4 illustrates a simplified Block Diagram of the detector system of FIG. 3.

Figure 5A:
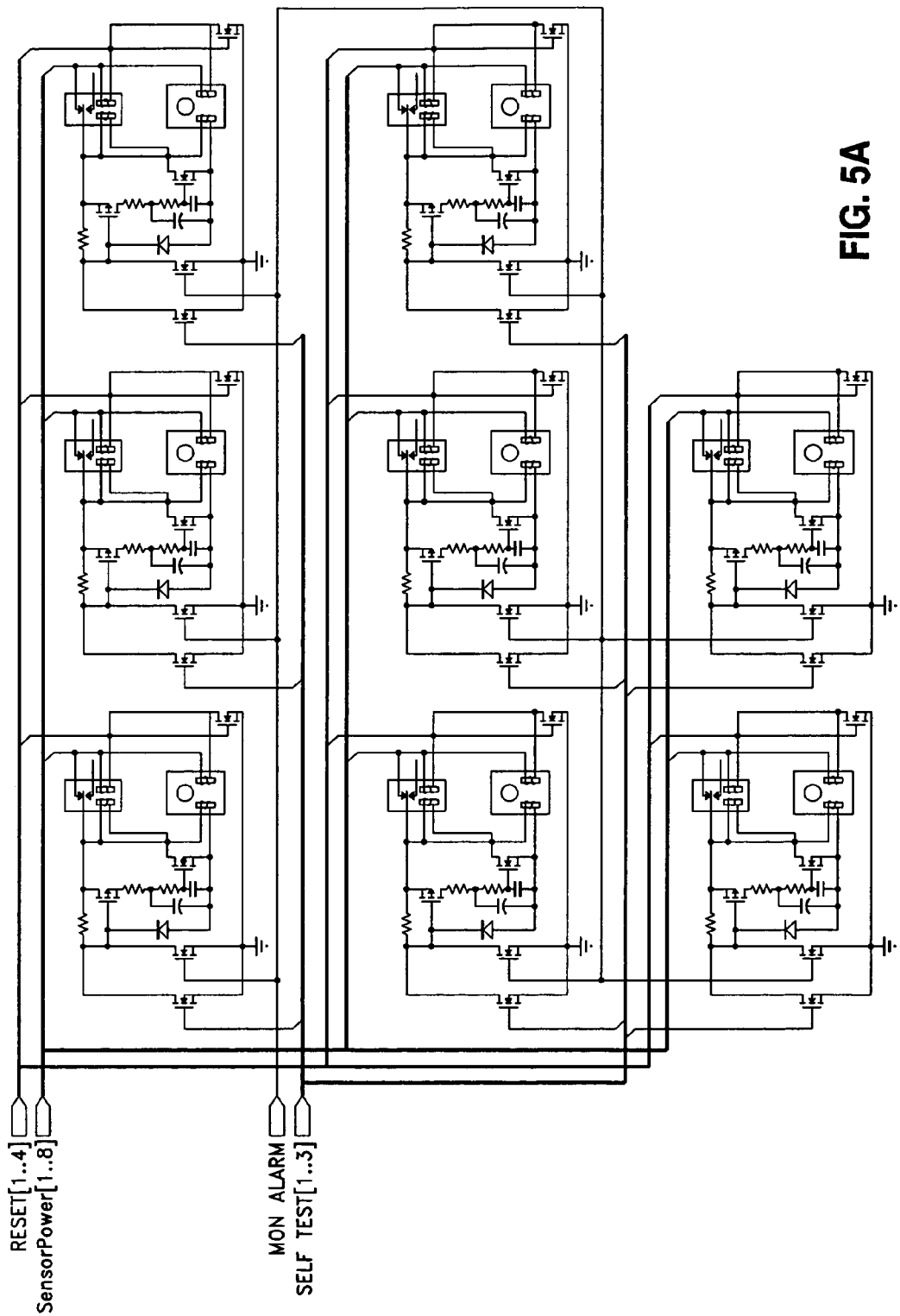
FIG. 5A shows circuit diagrams of the MON latching indicator drivers of the leak detector system of FIGS. 3-4.
Figure 5B:
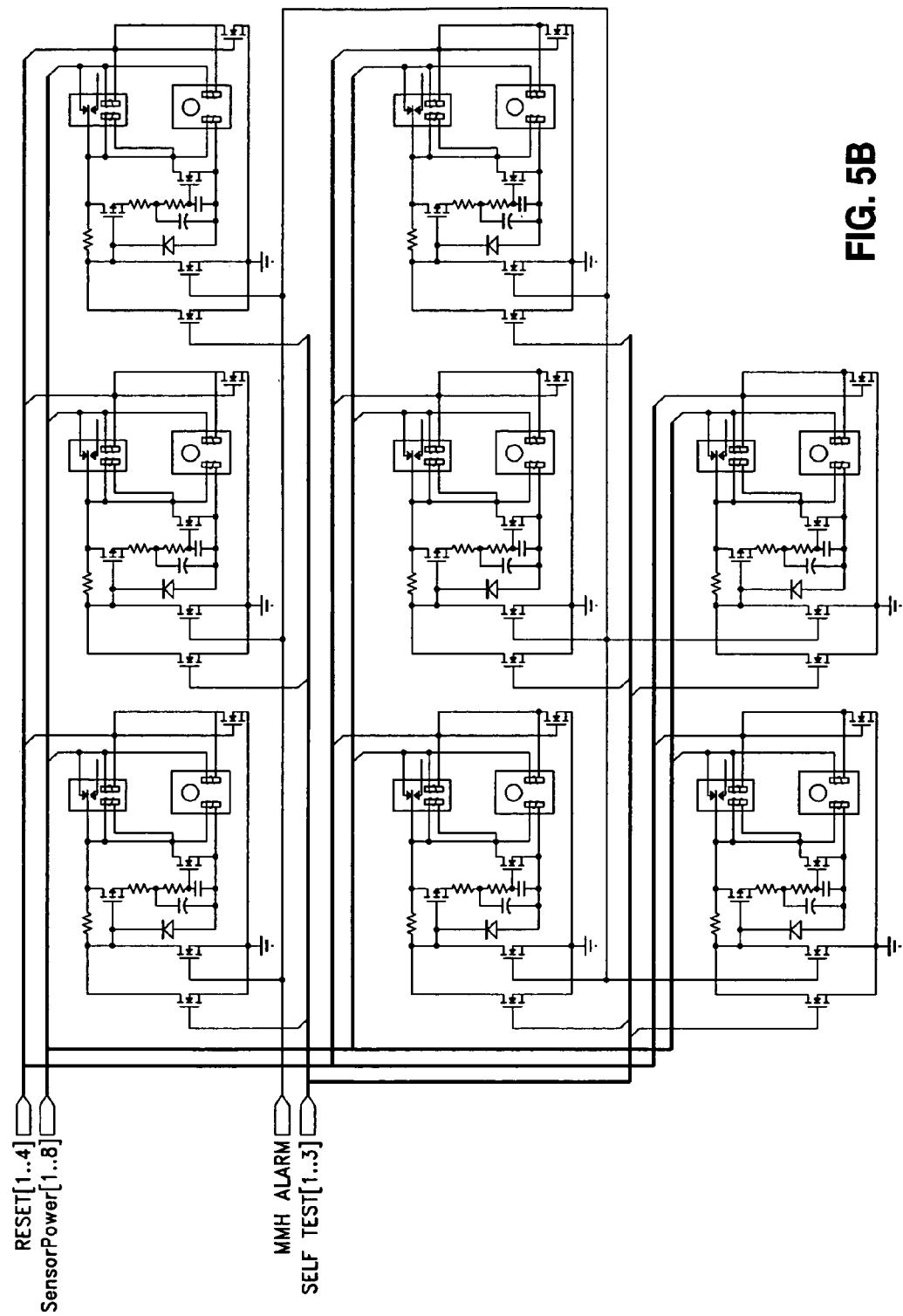
FIG. 5B shows a circuit diagram of MMH latching indicator drivers of the leak detector system of FIGS. 3-4.
Figure 5C:
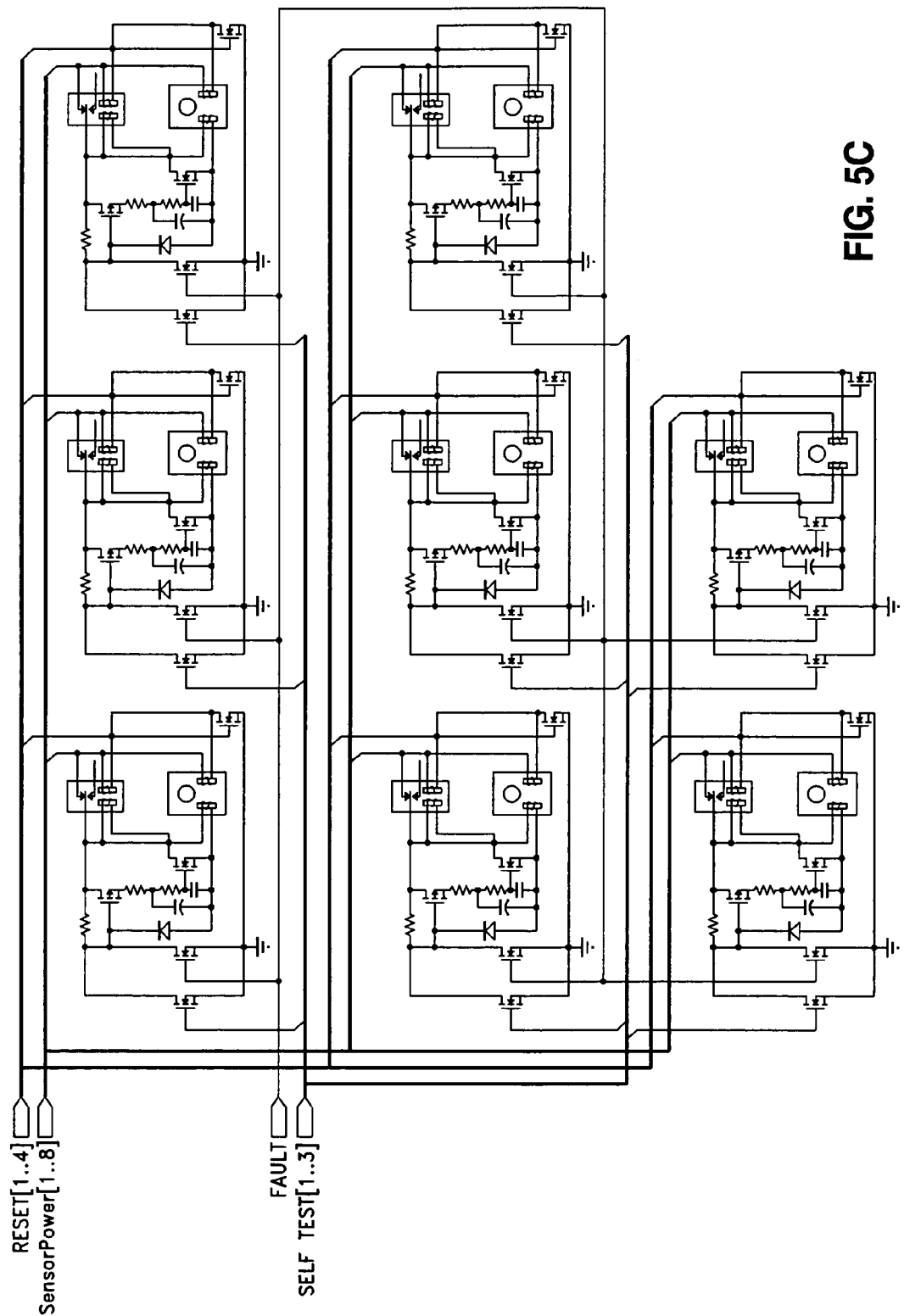
FIG. 5C shows circuit diagrams of the fault latching indicator drivers of the leak detection system of FIGS. 3-4.

FIG. 5A shows circuit diagrams of the MON latching indicator drivers of the leak detector. FIG. 5B shows circuit diagrams of the fault latching indicator drivers of the leak detectors. FIG. 5C shows a circuit diagram of MMH latching indicator drivers of the leak detector.

Figure 6A:
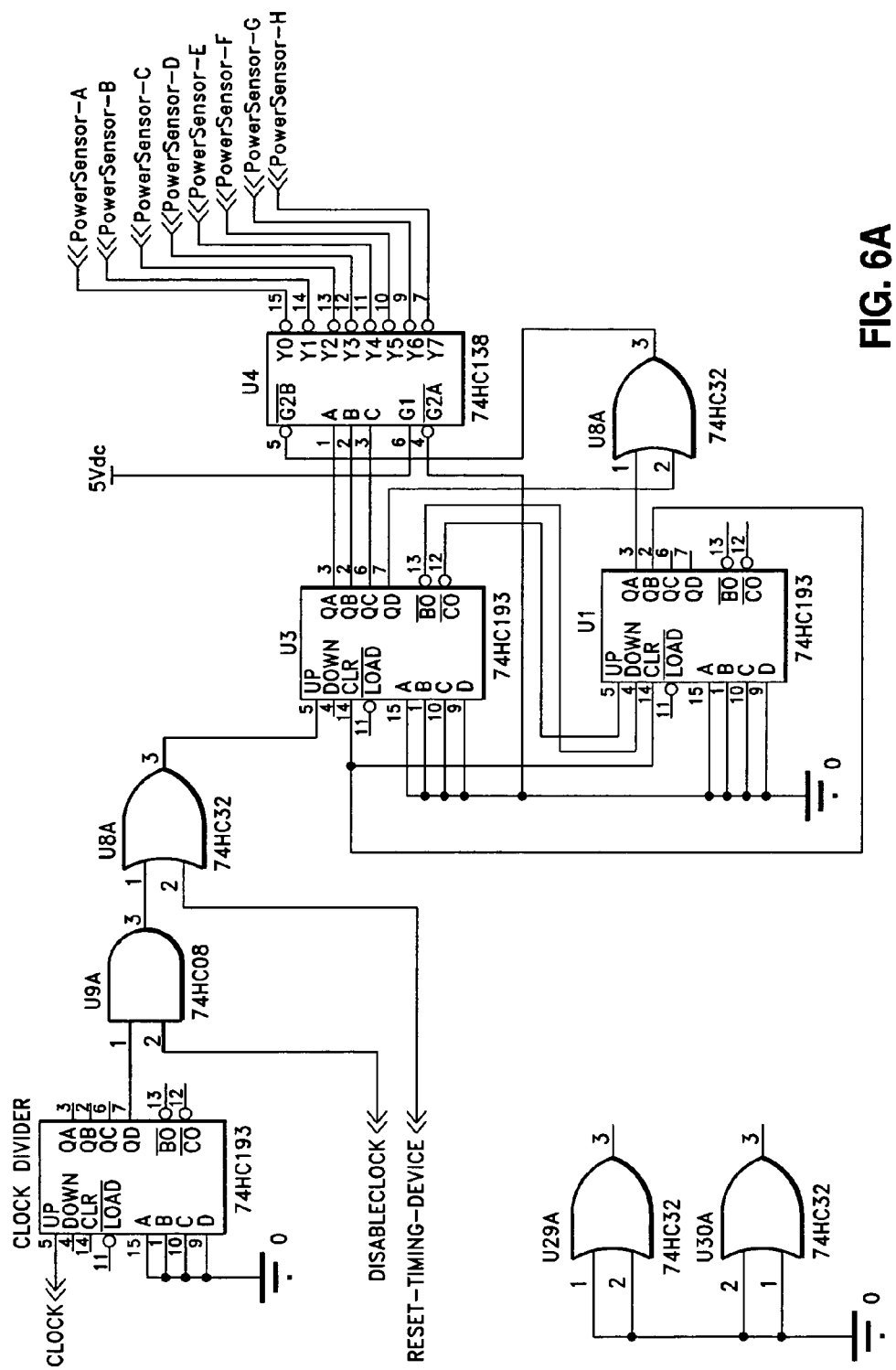
FIG. 6A shows a first portion of the controller circuit of the leak detector system of FIGS. 3-4.
Figure 6B:
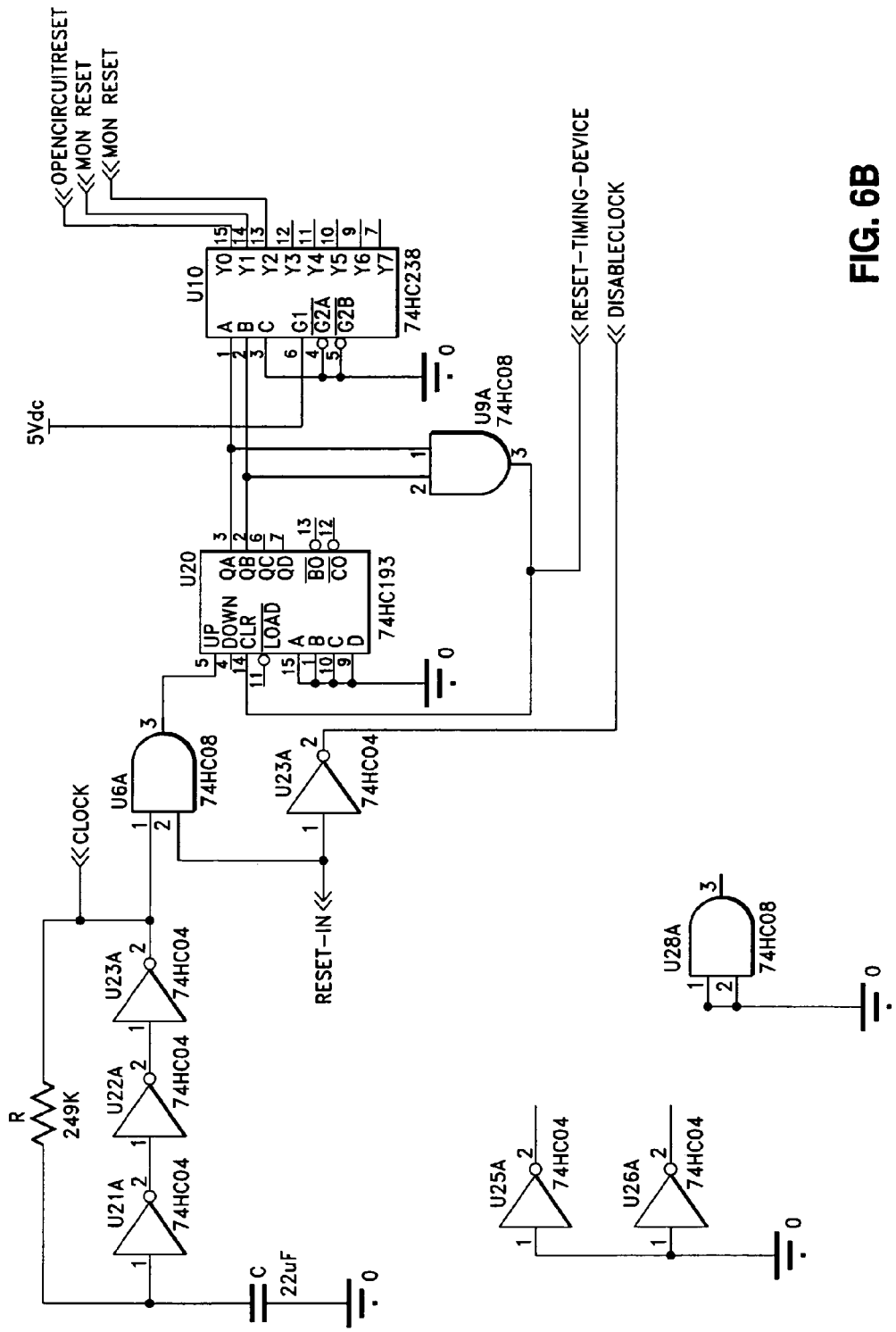
FIG. 6B shows a second portion of the controller circuit of the leak detector system of FIGS. 3-4.

FIG. 6A shows a first portion of the controller circuit of the leak detector. FIG. 6B shows a second portion of the controller circuit of the leak detector.

The control module monitors the detector system and activates an alarm module once the detector response exceeds a preset value. The control module also includes a central control and alarm, conditions power from station power (120/240 VAC or battery), collects detector output. In embodiments featuring multiple detector heads, the control module sequences power to each detector head.

The controller circuit provides a remote alarm and provides alarm alerts to area personnel specific to the fuel component leaking. The controller circuit also provides lapse time from alarm condition, nonvolatile fault and alarm indication, and 60 minutes of audio and visual alarm.

Figure 7:
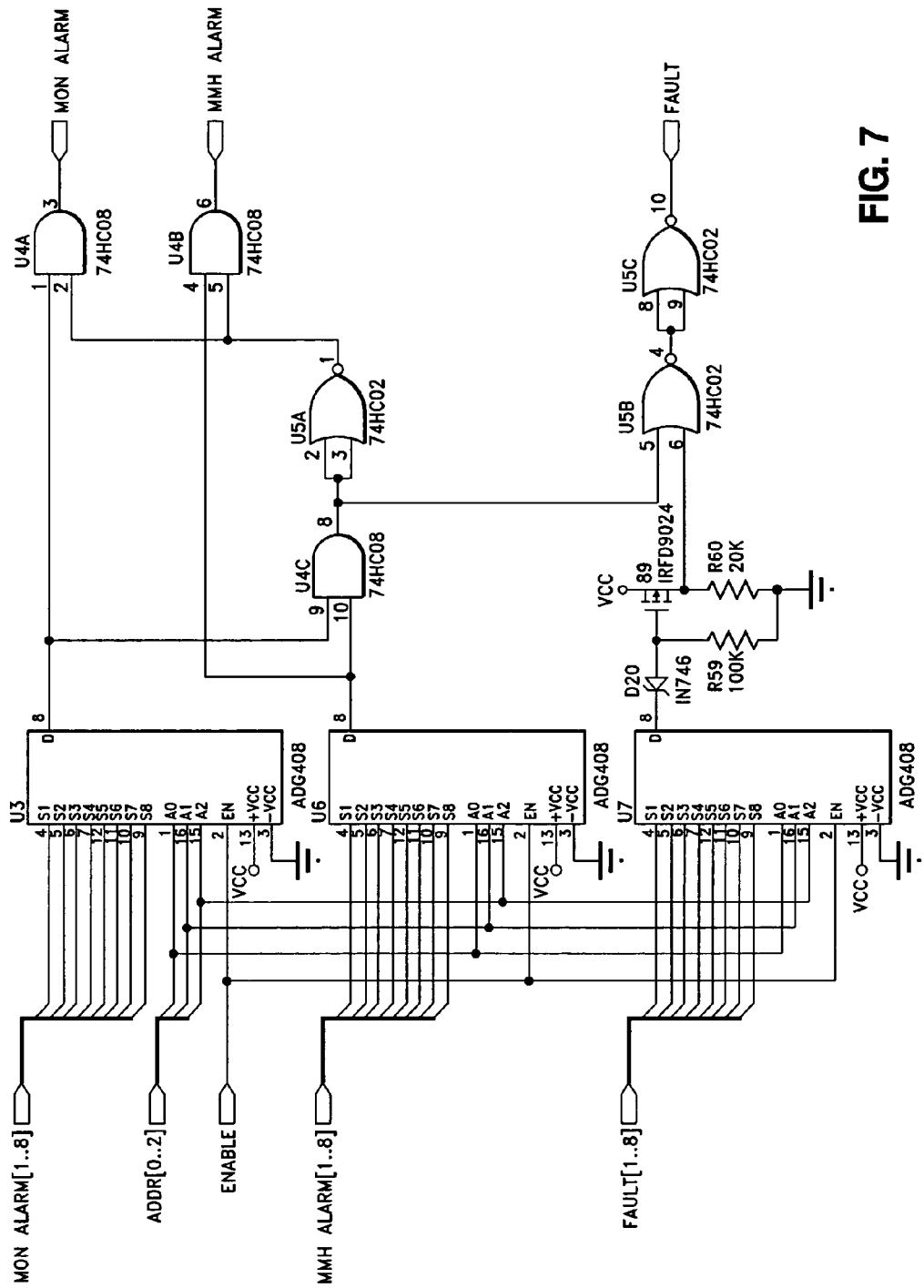
FIG. 7 shows a circuit diagram of the fault detector system of the leak detector system of FIGS. 3-4.

The control module also checks for operational conditions of each detector head. FIG. 7 shows a circuit diagram of the fault detection system of the leak detector.

Figure 8A:
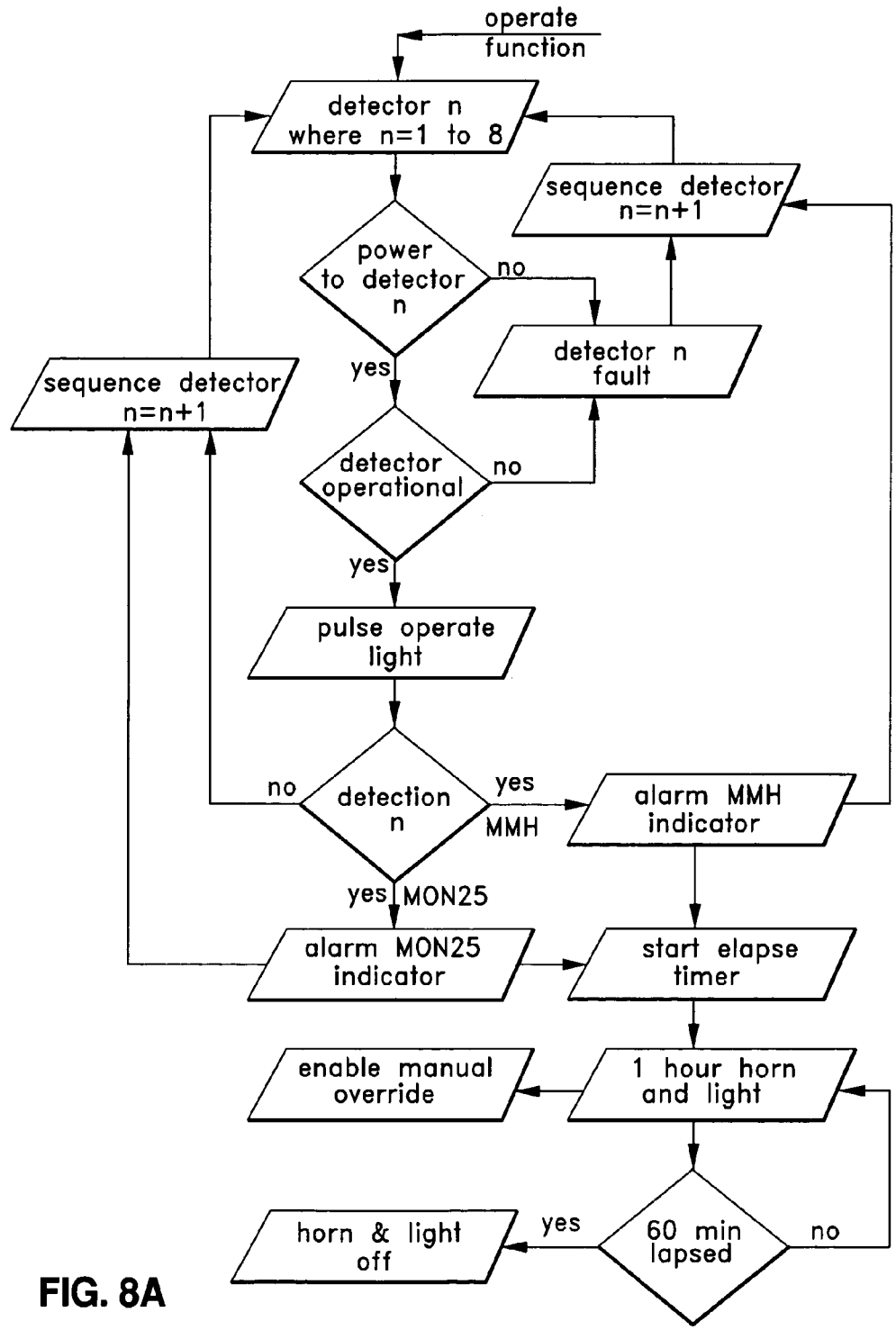
FIG. 8A is a simplified flow diagram illustrating logic operation of the hypergolic leak detector of the system of FIGS. 3-4.
Figure 8B:
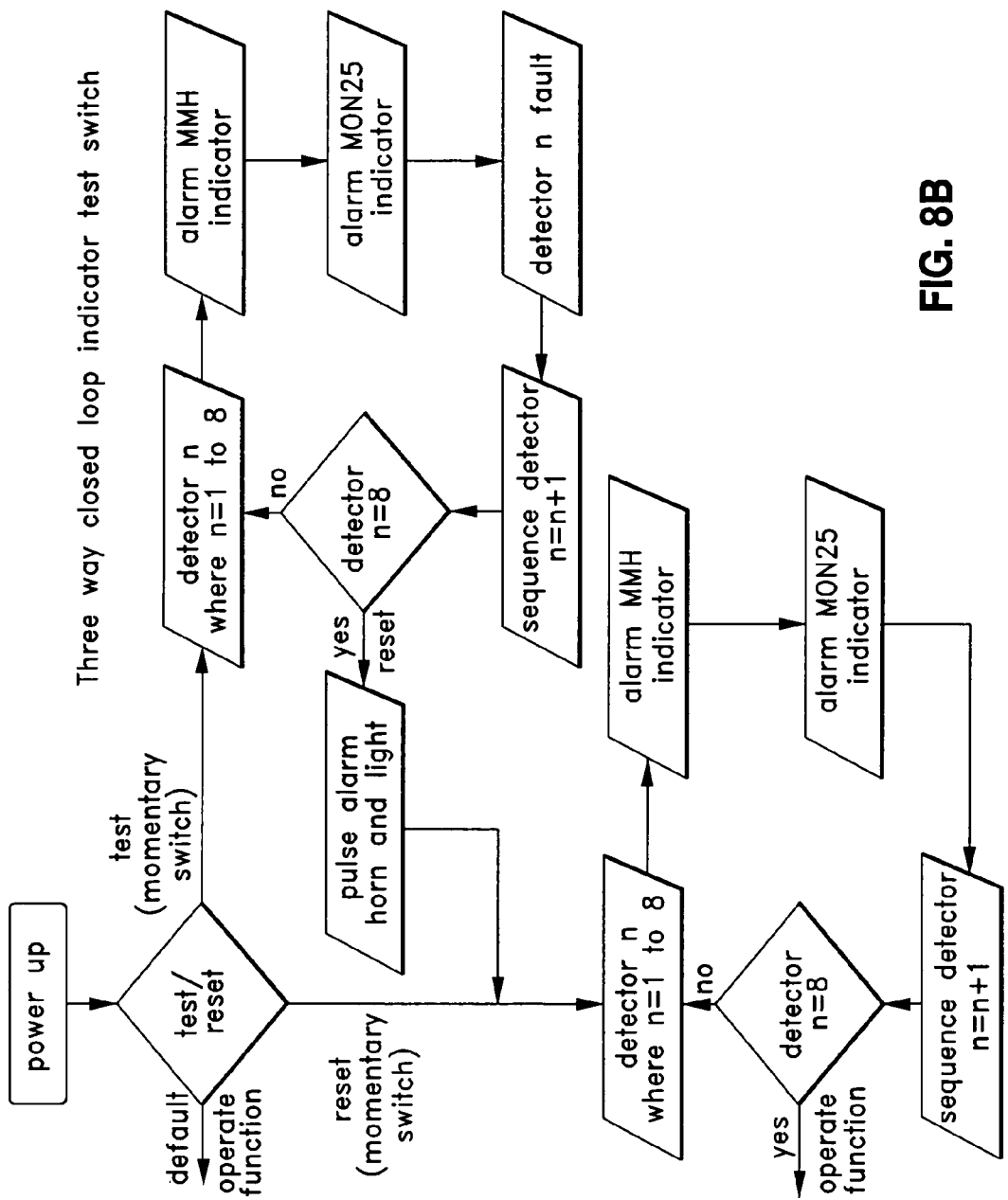
FIG. 8B is a simplified flow diagram illustrating operation of electrical and test feedback systems for the hypergolic leak detector of the system FIGS. 3-4.
Figure 8C:
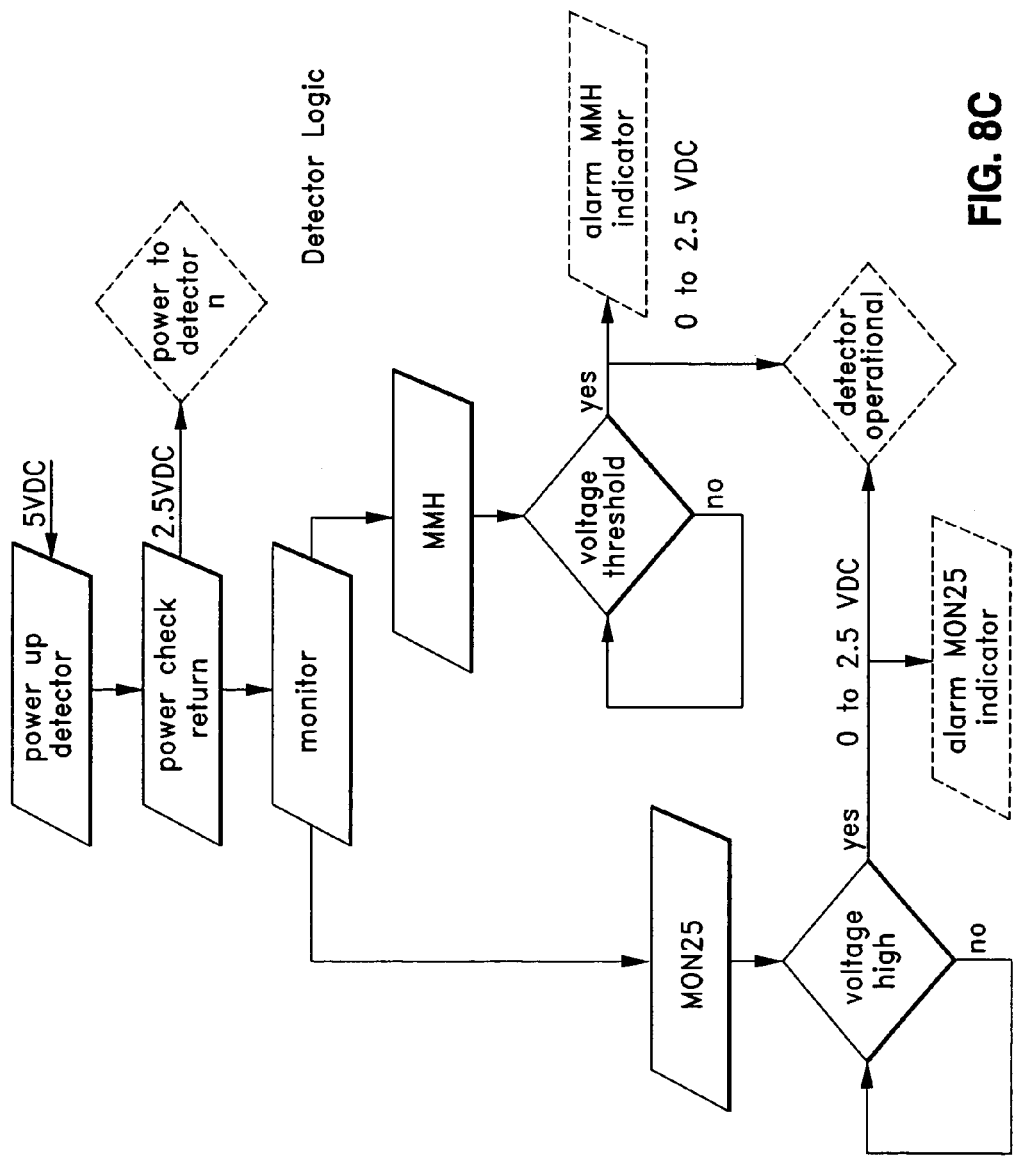
FIG. 8C is a simplified flow diagram illustrating interface of the detector of the hypergolic leak detector interface with the alarm module of FIGS. 3-4.

FIG. 8A provides a simplified flow chart of the overall logic for the embodiment of the detector system just described. FIG. 8B provides a simplified flow chart of the logic for electrical test and feedback systems of the detector. FIG. 8C provides a simplified flow chart of the logic for interface with an alarm module.

Figure 9A:
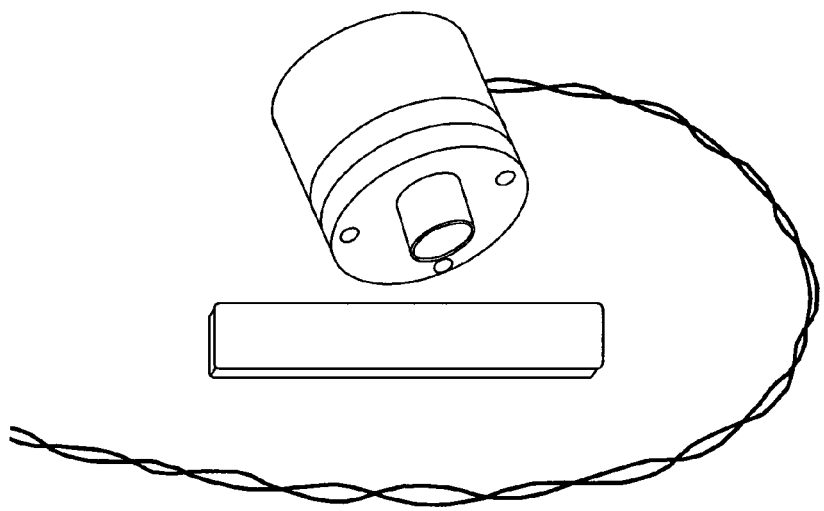
FIG. 9A is a perspective view of one embodiment of a leak detector in accordance with the present invention.

FIG. 9A is a perspective view of one embodiment of an optical detector head in accordance with the present invention. The detection head 900 is connected via umbilical cord 902 to control panel 904 shown in perspective view in FIG. 9B. In an embodiment in accordance with the present invention, up to eight detector heads can be connected and controlled by the control panel utilizing standard military connectors and cabling.

Figure 9B:
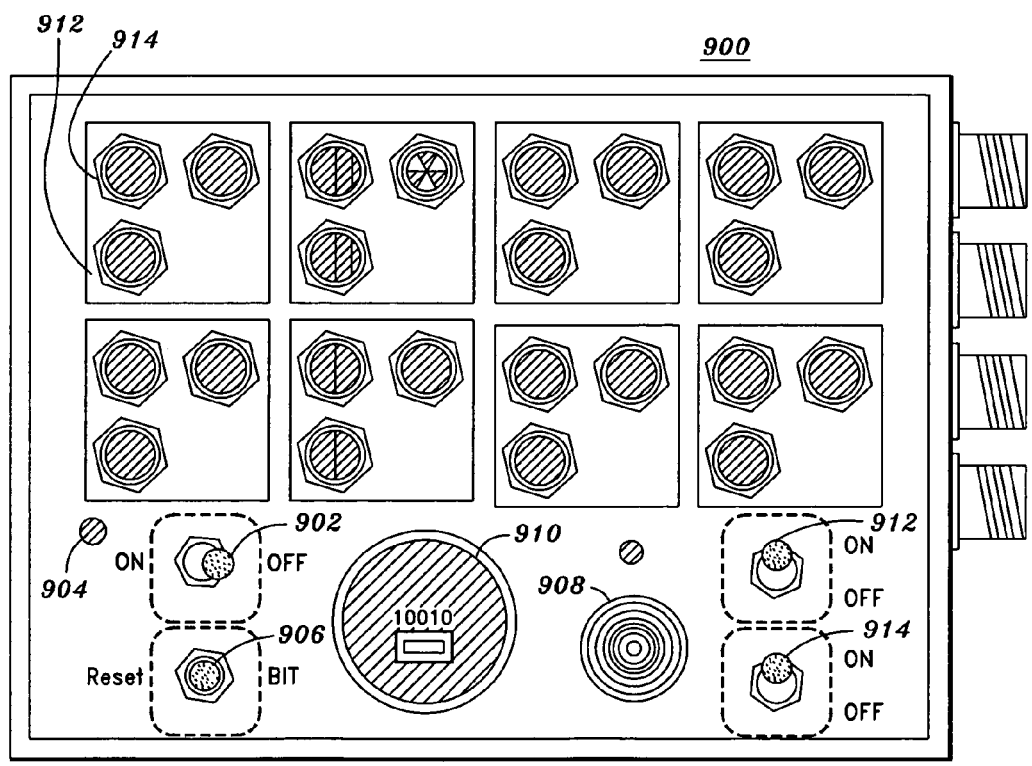
FIG. 9B is a frontal view of the embodiment of a leak detector shown in FIG. 9A.

The front view of the control panel illustrated in FIG. 9B. shows eight section panels 912 each having three latching indicators 914, one each for MMH, MON, and for fault. Control panel 900 further includes power switch 902 and power indicator light 904, and also includes test/reset switch 906. Control panel 900 also includes speaker 908 that serves as an audio indicator for an alarm event. Control panel 900 further includes timer 910 indicating the time from the last detected incident. Switches 916 and 918 may be employed to momentarily stop the alarm visual and audio alerts, or to acknowledge and turn off the visual and audio alarms.

While the above is a full description of specific embodiments in accordance with the present invention, various modifications, alternative constructions and equivalents may be used. For example, multiple detectors can be controlled and monitored by the system. In accordance with one embodiment of the present invention, a common control panel could be used to monitor leakage both optically and electrochemically.

Embodiments in accordance with the present invention offer a number of advantages over conventional detection systems. One such advantage is substantially reduced power consumption. Embodiments in accordance with the present invention may be operated on battery or station power, at 120/220 VAC. Embodiments may operate on extremely low power, for example at less than about 1 milliamps at 5 VDC. Battery operation can thus last for more than 30 days using a 7.5 amp hour battery.

Power conservation techniques that may be employed by systems in accordance with embodiments of the present invention include use of latching indicators and relays to require the pulsing of power only during transitions. CMOS circuitry may also be used to minimize current drain. In embodiments featuring multiple reader heads, power may be sequenced to each detector head at a low duty cycle in order to conserve power.

Other advantages of embodiments of methods and systems in accordance with the present invention include light weight and relatively small size. There are no known colorimetric detector systems of this size, owing in part to avoidance of the need for mechanical devices to unroll and then store as unrolled paper to serve as a record of past detected levels.

Still another advantage is the relatively simple architecture of the detection system, which increases its robustness and extends its environmental operation range. As illustrated by FIGS. 8B-C, the system also includes built-in testing for power and detector output.

Another advantage offered by embodiments of colorimetric detection devices in accordance with the present invention is the long-term stability of the chemical reagents used as part of the detector. The relative inertness and stability of these reagents in absence of hypergolic fuel components allows active monitoring using color change over an extended period and over a wide range of temperature and environmental conditions expected to be encountered in military applications such as THAAD as well as non-military applications.

While the above-described system is principally designed to operate as a safety sensor for THAAD missile system to meet US transportation safety requirements, additional uses of the sensor system could include any propulsion systems in civilian and military rocket launch systems, satellite systems, and military munitions that utilize hypergolic or other fuels. The manufacture, transportation, and storage of hypergolic fuels could also utilize this technology to ensure safe operations.

Given the above detailed description of the present invention and the variety of embodiments described therein, these equivalents and alternatives along with the understood obvious changes and modifications are intended to be included within the scope of the present invention.

What is claimed is:

1. A fuel monitoring system for use in a transportation system, the fuel monitoring system comprising:
    a fuel leak detector comprising
    a colorimetric chemical monitor configured to change color in response to presence of a fuel, and
    an optical reader comprising
    a first optical detector configured to monitor a color of a first portion of the calorimetric chemical monitor based on an intensity of first reflected light from the colorimetric chemical monitor, and
    a second optical detector configured to monitor a color of a second portion of the colorimetric chemical monitor based on an intensity of second reflected light from the colorimetric chemical monitor; and
    an alarm system in electronic communication with the fuel leak detector and configured to provide an alarm when a color of the calorimetric chemical monitor changes by a predetermined amount,
    wherein there are different reagents in the first and second portions.

2. The system of claim 1 wherein the calorimetric chemical monitor comprises a porous substrate impregnated with mercurous chloride/methylcellulose reagent in either the first or second portion.

3. The system of claim 1 wherein the calorimetric chemical monitor comprises a porous substrate impregnated with N-phenylanthranilic acid/titanium dioxide reagent in either the first or second portion.

4. The system of claim 3 wherein a portion of the porous substrate is impregnated with mercurous chloride/methylcellulose reagent.

5. The system of claim 2 wherein the porous substrate comprises paper.

6. The system of claim 1 wherein the optical reader further comprises a light source configured to illuminate a first surface of a porous substrate impregnated with a first reagent reactive with a hypergolic fuel component, the light source further configured to illuminate a second surface of the porous substrate impregnated with a second reagent reactive with a hypergolic fuel component, wherein the first optical detector is configured to receive light reflected from the first surface of the porous substrate and, in response, output a first voltage proportional to the intensity of first reflected light, and wherein the second optical detector is configured to receive light reflected from the second surface of the porous substrate and, in response, output a second voltage proportional to the intensity of second reflected light, wherein the first surface is the first portion, and the second surface is the second portion.

7. The system of claim 6 wherein the light source comprises a light emitting diode configured to emit light having a wavelength of about 455 nm.

8. The system of claim 6 wherein the optical reader further comprises:
a first comparator comprising
a first input node configured to electrically communicate with the first optical detector,
a second input node configured to electrically communicate with a first reference voltage, the first reference voltage corresponding to a first voltage output by the first optical detector receiving light reflected from the first surface of the porous substrate in the absence of a hypergolic fuel component, and
a first output node configured to output a first output voltage proportional to a difference between voltages at the first and second input nodes;
and a second comparator comprising
a third input node configured to electrically communicate with the second optical detector,
a fourth input node configured to electrically communicate with a second reference voltage, the second reference voltage corresponding to a second voltage output by the second optical detector receiving light reflected from the second surface of the porous substrate in the absence of a hypergolic fuel component, and
a second output node configured to output a second output voltage proportional to a difference between voltages at the third and fourth input nodes.

9. The system of claim 8 wherein the alarm is configured to be triggered when the first output voltage appearing on the first output node of the first comparator exceeds a first threshold value or when the second output voltage appearing on the second output node of the second comparator exceeds a second threshold value.

10. The system of claim 8 further comprising a beam splitter configured to cause light from the source to illuminate separate portions of the porous substrate.

11. A method for detecting leakage of a hypergolic fuel system, the method comprising:

monitoring an intensity of first reflected light from a first portion of a colorimetric chemical monitor with a first optical detector of an optical reader;
monitoring an intensity of second reflected light from a second portion of the colorimetric chemical monitor with a second optical detector of the optical reader; and
determining a fuel leak when the intensity of first reflected light drops below a first predetermined threshold or when the intensity of second reflected light drops below a second predetermined threshold,
wherein there are different reagents in the first and second portions.

12. The method of claim 11 wherein the calorimetric chemical monitor comprises a porous substrate impregnated with mercurous chloride/methylcellulose reagent in either the first or second portion.

13. The method of claim 11 wherein the calorimetric chemical monitor comprises a porous substrate impregnated with N-phenylanthranilic acid/titanium dioxide reagent in either the first or second portion.

14. The method of claim 11 wherein the colorimetric chemical monitor comprises a porous substrate impregnated with N-phenylanthranilic acid/titanium dioxide reagent, and wherein a portion of the porous substrate is impregnated with mercurous chloride/methylcellulose reagent.

15. The method of claim 14 wherein the porous substrate comprises paper.

16. The method of claim 11 further comprising:
illuminating, with a light source, a first surface of a porous substrate impregnated with a first reagent reactive with a hypergolic fuel component;
illuminating, with the light source, a second surface of the porous substrate impregnated with a second reagent reactive with a hypergolic fuel component;
receiving, with the first optical detector, light reflected from the first surface of the porous substrate;
receiving, with the second optical detector, light reflected from the second surface of the porous substrate;
outputting, with the first optical detector, a first voltage proportional to the intensity of first reflected light in response to the receiving, with the first optical detector; and
outputting, with the second optical detector, a second voltage proportional to the intensity of second reflected light in response to the receiving, with the second optical detector,
wherein the first surface is the first portion, and the second surface is the second portion.

17. The method of claim 16 wherein the illuminating, with a light source, a first surface comprises emitting, with a light emitting diode, light having a wavelength of about 455 nm.

18. The method of claim 16 wherein determining a fuel leak comprises:
providing a first reference voltage to a first input node of a first comparator, the first reference voltage corresponding to a first voltage output by the first optical detector receiving light reflected from the first surface of the porous substrate in the absence of a hypergolic fuel component;
providing a second reference voltage to a third input node of a second comparator,
the second reference voltage corresponding to a second voltage output by the second optical detector receiving light reflected from the second surface of the porous substrate in the absence of a hypergolic fuel component;
providing the first voltage output by the first optical detector receiving light reflected from the first surface of the porous substrate from the first optical detector to a second input node of the first comparator;

providing the second voltage output by the second optical detector receiving light reflected from the second surface of the porous substrate from the second optical detector to a fourth input node of the second comparator;

measuring a first output voltage produced at a first output node of the first comparator; and measuring a second output voltage produced at a second output node of the second comparator.

19. The method of claim 11 further comprising generating an alarm when a fuel leak is determined.

* * * * *